United States Patent [19]

Brezinski

[11] Patent Number: 4,495,052

[45] Date of Patent: Jan. 22, 1985

[54] REPLACEABLE JUNCTIONS FOR REFERENCE ELECTRODES

[75] Inventor: Donald P. Brezinski, Millis, Mass.

[73] Assignee: Corning Glass Works, Corning, N.Y.

[21] Appl. No.: 609,597

[22] Filed: May 14, 1984

Related U.S. Application Data

[63] Continuation-in-part of Ser. No. 419,001, Sep. 9, 1982, abandoned, which is a continuation-in-part of Ser. No. 218,788, Dec. 22, 1980, abandoned.

[51] Int. Cl.³ .............................................. G01N 27/30
[52] U.S. Cl. .................................................... 204/435
[58] Field of Search ...................... 204/435, 403, 1 H; 324/438

[56] References Cited

U.S. PATENT DOCUMENTS

| | | | |
|---|---|---|---|
| 2,058,761 | 10/1936 | Beckman et al. | 204/435 X |
| 3,272,731 | 9/1966 | Hutchison et al. | 204/435 |
| 3,530,056 | 9/1970 | Haddad | 204/435 |
| 3,742,594 | 7/1973 | Kleinberg | 29/592 |
| 3,806,439 | 4/1974 | Light et al. | 204/435 |
| 4,116,798 | 9/1978 | Magar et al. | 204/435 |
| 4,166,020 | 8/1979 | Trampert | 204/435 X |
| 4,208,253 | 6/1980 | Formaro et al. | 204/1 T |
| 4,278,519 | 7/1981 | Won | 204/435 |

FOREIGN PATENT DOCUMENTS

| | | | |
|---|---|---|---|
| 1391979 | 2/1965 | France | 204/435 |
| 729575 | 5/1955 | United Kingdom | 204/435 |

Primary Examiner—G. L. Kaplan
Attorney, Agent, or Firm—W. E. Maycock

[57] ABSTRACT

In a reference electrode comprising an enclosure containing a half-cell electrode, a half-cell electrolyte, and a reference junction positioned in an outlet for the electrolyte, the half-cell electrode being connectable to an external measuring means, the improvement which comprises a removable and replaceable reference junction comprising a removable encasing body encasing a porous member, said porous member being in length only up to about one half the length of the encasing body, fixedly inserted through said outlet.

18 Claims, 7 Drawing Figures

U.S. Patent  Jan. 22, 1985  4,495,052

REPLACEABLE JUNCTIONS FOR REFERENCE ELECTRODES

This application is a continuation-in-part of application Ser. No. 419,001, filed Sept. 9, 1982 and now abandoned, which is a continuation-in-part of application Ser. No. 218,788, filed Dec. 22, 1980, now abandoned.

CROSS REFERENCE TO RELATED APPLICATION

U.S. patent application Ser. No. 218,789 filed on Dec. 22, 1980 and now abandoned, entitled "Replaceable Junctions for Reference Electrodes", filed in the name of R. L. Souza and assigned to the assignee of the instant application.

BACKGROUND OF THE INVENTION

The present invention is broadly concerned with reference electrodes, and the reference electrode portion of combination electrodes, which are employed to provide the stable reference potentials required by a variety of electroanalytical techniques, such as ion-selective electrode measurements, controlled potential coulometry, polarography, and the like. More particularly, the present invention is concerned with a reference electrode and the reference electrode portion of a combination electrode, each having an improved removable and replaceable junction.

A reference electrode most frequently is used in conjunction with an ion-selective electrode, either separately or in combination, to measure the activity (which is a function of concentration) of a given ion in a sample solution. Consequently, the discussion which follows primarily relates to such use. It is to be understood, however, that such discussion is not intended to in any way limit the spirit or scope of the present invention.

The two electrodes, i.e., the reference electrode and the ion-selective electrode, both of which are immersed in the sample solution, typically are connected to a means for measuring the potential difference between the two electrodes, e.g., an electrometer. The reference electrode provides a constant electromotive force or potential against which the potential of the ion-selective electrode is compared. The latter potential consists of a constant component from the electrochemical half-cell of the ion-selective electrode and a variable component which is the potential across the sensing membrane and which is dependent upon the activity (concentration) of the ion being measured. The variable component, then, is readily correlated with ion activity (concentration) by known means. To give accurate results, the potential of the reference electrode should not change with the composition of the sample.

The reference electrode is designed to be minimally sensitive to changes in the external, sample ionic environment. It consists of at least three components: (1) a half-cell electrode (typically a silver-silver chloride mixture), (2) a half-cell electrolyte (typically 4M potassium chloride solution saturated with silver ions), and (3) a reference junction. The half-cell electrode and half-cell electrolyte constitute an electrochemical half-cell having a known, stable, constant electrical potential. Direct physical, and therefore electrical, contact between the half-cell electrolyte and the sample solution is established through the reference junction which usually consists of a porous ceramic plug, metal or asbestos fiber bundle, sintered plastic, or like means of achieving a fluid mechanical leak.

As used herein, the term "half-cell electrode" means the solid-phase, electron-conducting contact with the half-cell electrolyte, at which contact the half-cell oxidation-reduction reaction occurs which establishes the stable potential between the half-cell electrolyte and the contact.

Because the junction electrolyte and the measured sample usually differ in ionic strength and transference, a "liquid junction potential" typically develops across the reference junction. Variation in this junction potential from sample to sample is a source of error in electrode measurements, and one goal of reference electrode technology is to make the junction potential as small, stable, and reproducible as possible. But the reference junction, for various reasons usually involving clogging, can become wholly or partly inoperable. Clogging of junction pores by foreign materials disrupts the direct physical contact which is required to establish a stable, reproducible liquid junction potential between the internal and measured solutions. Also, clogging typically introduces fixed ionic charge into the junction, which causes an anomalous increase in junction potential in low-ionic-strength measurements. Also, in many reference electrode designs, the internal filling solution flows out of the reference electrode into the measured solution. I have found that this flow generally results in faster and more accurate response, since the flow serves to flush the previously measured solution more rapidly from the junction and also serves to increase the ionic strength at the junction surface, thereby reducing anomalies due to fixed space-charge in the junction. Clogging blocks this beneficial flow of junction electrolyte, leading to slower, less accurate measurements. Finally, clogging increases the electrical resistance of the junction, which causes a proportionate increase in the electrical noise of the measurement. Thus, typical symptoms of a clogged junction include slow, erratic, noisy, and often erroneous response.

Junction clogging may arise from a variety of sources, both extrinsic and intrinsic. For example, the proteins and lipids present in many measured samples tend, because of electrostatic and hydrophobic forces, to bind to and permeate many junction materials. Also, certain components of the filling solution tend to precipitate upon coming into contact with the measured solution within the junction. For example, AgCl and $Ag_2S$ tend to precipitate within the junction of Ag-/AgCl reference electrodes immersed in dilute chloride- and sulfide-containing samples, respectively.

In the prior art, failure of the reference junction has usually meant replacement of the entire reference electrode, an expensive, undesirable solution where the reference junction is often the least expensive component of the reference electrode. Attempts to replace the reference junction by the laboratory practitioner have usually ended in failure, since in most high-quality electrodes, the junction is permanently fused or cemented to the electrode body. Even in electrode designs where the junction is held within an orifice by friction or pressure alone, the junction is typically too fragile to withstand the forces required for removal or insertion. Finally, ven if the junction could be removed by force, some portion of the porous junction material would have to extend beyond the electrode body to allow traction. But, I have found that protrustion of the porous material into the measured solution may contribute somewhat to a low and inaccurate response by introducing an element of spherical rather than planar diffusion. A flat junction surface is preferable, which is incompatible with protrusion of the porous member.

Turning now to the known prior art, a 1979 Graphics Controls catalog shows a commercially available renewable junction electrode. A new junction is created by pulling the threadlike woven fiber junction to expose a fresh increment. When the built-in supply of woven fiber junction is exhausted, the entire electrode must be replaced.

U.S. Pat. No. 4,282,081 discloses a double junction reference electrode having a removable sealing plug at the lower end of the lower or external junction electrolyte compartment, which plug contains a conduit extending axially through the plug and providing a flow-restrictive fluid permeable path between the lower compartment and a test system external of the electrode, i.e., an outer liquid junction. The conduit or outer junction preferably is made of porous ceramic. Thus, the outer junction is replaceable only by replacing a portion of the electrode, i.e., the removable sealing plug. According to the patent, the electrode components are separable at threaded junctions to allow easy access to the internal chambers for thorough cleaning and convenient refilling. There is no recognition in the patent regarding outer junction clogging or the problems associated therewith, and no indication that an ability to replace the outer junction is advantageous. Furthermore, such replacement, if actually done, requires replacement of the removable sealing plug which contains the outer junction. Moreover, the need to replace the entire plug prevents the use of such a concept in a combination electrode, an inherent disadvantage. As already noted, however, cleaning and refilling are the only reasons cited for dismantling the electrode.

U.S. Pat. No. 2,058,761 relates to an apparatus for testing acidity. The apparatus includes two electrodes, one of which comprises a glass tube open at both ends but tapered inwardly at the lower end to constitute a seat portion of frustro-conical shape, in which lower end there rests a frustro-conical plug. While the plug prevents practically all leakage of fluid from the tube, there always is present a thin film of solution between the surfaces of the plug and the tube to provide ready conduction of current between the solution to be tested and the electrolyte contained in the tube. The composition of the plug is not specified.

U.S. Pat. No. 3,530,056 discloses a flexible liquid junction which includes a flexible, electrically insulating sheath, within which is disposed at one end an electrically insulating porous plug and a wettable wicking which extends from the plug to the other end of the sheath. The plug can be a porous ceramic. The patent neither teaches nor implies that such flexible liquid junction is removable and replaceable.

SUMMARY OF THE INVENTION

Figure 1:
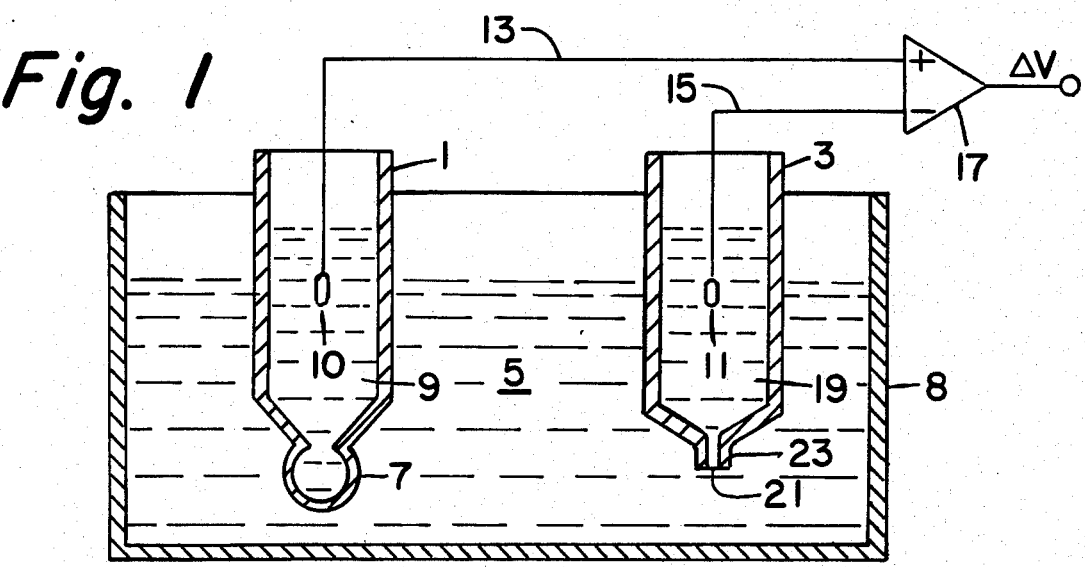
FIG. 1 of the drawing is a schematic of a typical pH measurement system, illustrating the essential components thereof.

It is an object of this invention to provide an improved reference electrode.

A more specific object of this invention is to provide a reference electrode including an improved replaceable reference junction.

Another object of this invention is to provide a reference junction of design and strength capable of being removed and replaced by the laboratory practitioner or equipment operator with simple laboratory tools.

Still another object of this invention is to provide a replaceable reference junction which improves equipment performance.

Other objects of the invention will be apparent to the skilled artisan from the detailed description of the invention hereinbelow.

In accordance with the present invention, there is provided a reference electrode comprising an enclosure containing a half-cell electrode, a half-cell electrolyte, and a reference junction positioned in an outlet for the electrolyte, the half-cell electrode being electrically connectable to an external measuring means, said reference junction being removable and replaceable. More specifically, the reference electrode comprises a sealing grommet positioned tightly in the electrolyte outlet and around which liquid flow essentially does not occur, with the grommet having at least one eyelet through which the removable and replaceable reference junction can be inserted and removed. The reference junction comprises a capillary tube encasing a porous medium, such as a porous ceramic rod, shorter than the tube and positioned in the tube toward the terminus of the tube which will extend into a sample solution. Liquid flow does not essentially occur around the capillary tube positioned through the grommet. As used herein, the term "porous ceramic" means a porous, rigid, nonmetallic solid prepared by the sintering or firing of one or more inorganic precursors.

In a preferred embodiment of the present invention, one end of the porous member is positioned in the capillary tube so as to be flush with an end of the capillary tube and to extend through the tube up to about one half of the length of the tube, preferably up to about one third of the length of the capillary tube.

In another preferred embodiment of the present invention, a pH or other ion-selective sensing bulb also extends through the grommet in a combination electrode configuration.

DETAILED DESCRIPTION OF THE INVENTION

As already noted, the term "porous ceramic" is used herein to mean a porous, rigid, nonmetallic solid prepared by the sintering or firing of one or more inorganic precursors. In a preferred embodiment, such nonmetallic solid is substantially crystalline. In another preferred embodiment, such inorganic precursors are particulate.

The porous ceramic which is used in the present invention generally is prepared in accordance with methods which are well known to those having ordinary skill in the art. The inorganic precursors also are well known to those having ordinary skill in the art. By way of illustration only, some examples of suitable inorganic precursors include silica, silica-based glasses, feldspar, alumina, clays, and the like.

FIG. 1 shows the elements of a pH measurement system. A pH electrode 1 and reference electrode 3 are partially immersed in sample solution 5 inside of container 8 and both electrodes are electrically connected by conductors 13 and 15 to electrometer 17. The potential across the glass sensing-membrane 7 changes in proportion to differences in pH between external sample solution 5 and a pH buffer solution 9 contained within the sensor membrane. An electrochemical half-cell 10 is used to establish a stable electrical connection between the buffer solution and the wire conductor going to the electrometer. This half-cell has a fixed potential determined by the chloride ion concentration of the buffer. The difference in potential between the external solution 5 and the positive electrometer terminal now changes with pH, and it is this change in potential that is to be monitored. The role of the reference electrode is to establish a fixed half-cell potential between the external measured solution and the negative electrometer terminal. In measurements of unknown solutions, the half-cell cannot be directly immersed in the sample, since its potential will vary with the unknown anionic, e.g., chloride ion, activity of the solution. Therefore, an indirect reference connection is made by immersing the reference half-cell 11 into a known electrolyte 19 (usually AGCl-saturated 4M KCl), and then establishing physical and electrical contact between this electrolyte and the measured solution through a reference junction 21 positioned in outlet 23. The reference junction usually consists of a porous ceramic plug, asbestos fiber, or other means of achieving a fluid mechanical leak. The reference junction functions primarily as a flow restrictor and filtration member, and also serves to define the shape of the interface between the solutions. Ideally, the junction is sufficiently porous to allow a low resistance contact, preferably well below 10K ohm, between the external and internal solutions, but is not so porous that the solutions become mutually contaminated.

Figure 2:
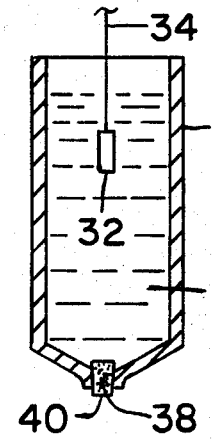
FIG. 2 of the drawing depicts in cross section a conventional reference junction positioned in a reference electrode.

FIG. 2 is a detailed cross-sectional view of a conventional reference electrode.

Figure 3:
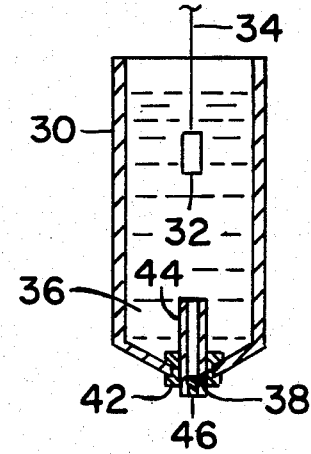
FIG. 3 of the drawing depicts in cross section a reference junction of the present invention positioned in a reference electrode.

FIG. 3 is a detailed cross-sectional view of the reference electrode of FIG. 2, but including a reference junction as in the present invention.

In FIGS. 2 and 3, reference electrode 30 includes electrochemical half-cell 32, electrical conductor 34, electrolyte solution 36 and outlet 38 through which the reference junction will communicate with the sample solution, not shown. In FIG. 2, ceramic plug 40 is inserted into outlet 38, while in FIG. 3, a grommet 42 is fixedly inserted into the outlet, through which there is found hollow glass capillary tube 44 having porous ceramic plug 46 encased therein and extending about one third of the way up the tube. The tube and encased plug comprise the replaceable reference junction per se of this invention.

Figures 4, 7:
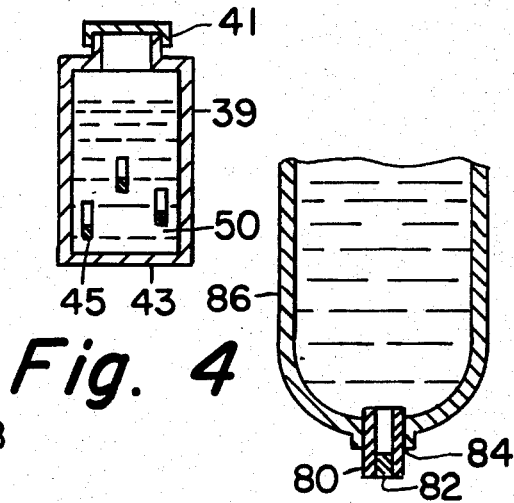
FIG. 4 of the drawing depicts in cross section a plurality of replaceable junctions of the present invention in a shippable container.
FIG. 7 depicts in partial cross section an alternative design exemplifying the present invention.

FIG. 4 depicts in cross section a shipping container 39 formed of mating screw cap lid 41 and body 43, in which there is placed a plurality of replaceable junctions 45 of the present invention. In the shipping container, the replaceable junctions are completely immersed in solution 50, which is preferably the inner electrolyte into which the reference junction will be inserted so that an equilibration time is not required when the junction is inserted into the reference electrode.

Figure 5:
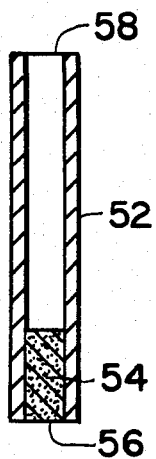
FIG. 5 of the drawing depicts in cross section an enlarged view of the reference junction of the present invention.

FIG. 5 depicts a preferred embodiment of the improved replaceable junction of the present invention in which glass capillary tube 52 of about two millimeters in outside diameter, about one millimeter in internal diameter and about twelve millimeters long is employed as the encasing sheath. A porous ceramic plug 54, about one millimeter in diameter and about 3 millimeters long is inserted into one end of the 12 millimeter long tube. A high flame, say about 1250° C., is run over the outside of the tube encasing the ceramic to seal or clad the glass to the ceramic. Thereafter, end 56 of the tube is ground flat to the ceramic and end 58 is firepolished or beveled to facilitate insertion into the grommet. Where desired, annealing of the cladding can be carried out.

Figure 6:
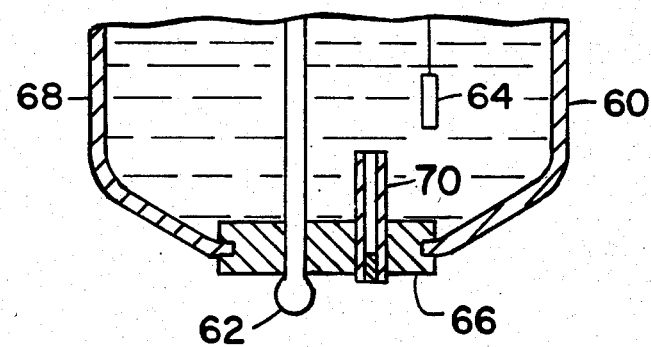
FIG. 6 depicts a partial cross section of a combination electrode with the junction of the present invention.

FIG. 6 is a cross section of the lower end of a combination electrode 60 where both glass electrode 62 and reference junction 70 extend through grommet 66. Junction electrolyte 68 is contained within the combination electrode body. Reference half-cell 64 extends into this electrolyte. Reference junction 70 extends through the grommet.

Furthermore, since a general feature of the present invention is the encasing of the porous junction member within an encasing body which facilitates its removal and insertion into the body of the reference electrode, this may be achieved by means other than those illustrated above. For example, rather than affixing the grommet to the electrode body, grommet means could be incorporated as an integral part of the removable encasing body.

In a further example, no grommet would be used, but either the removable encasing body itself or the reference electrode orifice would be made of a slightly compressible material, e.g., polypropylene, allowing a tight, leak-free fit between the junction-encasing body and electrode body. In FIG. 7, removable polypropylene encasing body 80 for porous ceramic member 82 fits tightly into glass orifice 84 formed in electrode body 86.

R. L. Souza, in application Ser. No. 218,789, has invented a replaceable reference junction which differs from the present invention in that in Souza's preferred embodiment the filtration member is of the same length as the glass capillary tube, that is the filtration member is coextensive from end to end with the capillary tube. The design of the present invention responds much more rapidly than Souza's because I have found that the maximal time for a solution to diffuse out of the filtration member, and hence the electrode response time, increases as a function of the square of the length of the filtration member, with or without outward flow. A second improvement over Souza's design is lowered electrical noise sensitivity of the reference electrode of this invention. A long porous member, such as a ceramic porous plug, often has excessive electrical resistance and the electrical noise sensitivity of a reference electrode is directly proportional to its electrical resistance, which is most cases is contributed almost entirely by the reference junction. Finally, upon initial hydration, air tends to become trapped within the excessive length of ceramic used in Souza's preferred embodiment, often resulting in a poor or open electrical connection between the sample solution and the half-cell electrolyte of the reference electrode. The shorter ceramic junction of the present invention hydrates more readily and reliably.

In the present invention, the long capillary tube provides sufficient strength and handling ability while the length of the shorter filtration member can be varied for optimum performance. With Corning Glass Works high flow ceramic No. 003798, a three millimeter length thereof encased within a 12 millimeter long glass capillary tube has been found to give good performance in most applications. More generally, the length of the ceramic plug typically will be in the range of from about 1 to about 5 millimeters, with the cladding typically having a length of from about 10 to about 20 millimeters.

Variations of the present invention will be apparent to the skilled artisan. For example, any porous member used as a junction in reference electrodes in the art should be usable in the present invention, as long as a compatible casing is known. For example, some porous members might not be usable where the glass tube is to be fired, but a plastic casing flowing at lower temperature or sealable by means of a softening solvent or epoxy cement could be employed, for example, a porous polypropylene or polyvinylidene plug encased at the end of a non-porous tube of the same composition. It is possible for the porous member to extend out of the encasing sheath, although such a configuration is not preferred. Also, when used, the reference junction preferably should extend beyond the grommet in both directions, and it is preferred that the filtration member end of the reference junction extend sufficiently past the bottom of the grommet so that it can be grasped by tweezers or other simple laboratory tool for removal, while the other end of the reference junction extends into the internal electrolyte solution. Furthermore, although the present invention has been illustrated by means of single junction reference electrode embodiments, the present invention is also applicable to double junction reference electrodes where the reference junction of the present invention would preferably be used as the outer reference junction between the outer electrolyte and sample solution, although it could also be used as the internal (inner) junction, between the half-cell electrolyte and outer electrolyte, particularly in pull-apart electrode designs.

The present invention is usable with the variously employed electrochemical half-cells, such as silver-silver chloride, calomel and so forth, and could be usable even with gelled internal electrolytes.

What is claimed is:

1. In a reference electrode comprising an enclosure containing a half-cell electrode, a half-cell electrolyte, and a reference junction positioned in an outlet for the electrolyte, the half-cell electrode bing connectable to an external measuring means, the improvement which comprises a removable and replaceable reference junction comprising a removable glass encasing body encasing a porous member which is a porous ceramic, said porous member being in length only up to about one half the length of the glass encasing body, fixedly inserted through said outlet which comprises a compressible grommet, in which said glass encasing body is glass capillary tubing bonded to said porous member, said reference junction being removable and replaceable by the laboratory practitioner with simple laboratory tools.

2. The reference electrode of claim 1 wherein the removable encasing body is essentially a cylindrical tube.

3. The reference electrode of claim 2 wherein the porous member has a length only up to one third the length of the removable encasing body.

4. The reference electrode of claim 3 wherein the entire porous member is encased within the removable encasing body.

5. The reference electrode of claim 4 in which the length of said porous member is in the range of from about 1 to about 5 millimeters and the glass tubing has a length of from about 10 to about 20 millimeters.

6. The reference electrode of claim 3 wherein the entire porous member is encased within the removable encasing body and one end thereof is flush with one end of the removable encasing body.

7. The reference electrode of claim 6 in which the length of said porous member is in the range of from about 1 to about 5 millimeters and the glass tubing has a length of from about 10 to about 20 millimeters.

8. The reference electrode of claim 3 wherein the entire porous member is encased within the removable encasing body and one end thereof is flush with the removable encasing body, and the reference junction is positioned in the grommet so that the open end of the removable encasing body extends into the half-cell electrolyte.

9. The reference electrode of claim 3 wherein the entire porous member is encased within the removable encasing body and one end thereof is flush with the removable encasing body, and the reference junction is positioned in the grommet so that the open end of the removable encasing body extends into the half-cell electrolyte, and the end of the removable encasing body closed by the porous member extends beyond the exterior side of the grommet to be in contact with the sample solution.

10. The reference electrode of claim 1 in which the length of said porous member is in the range of from about 1 to about 5 millimeters and the glass tubing has a length of from about 10 to about 20 millimeters.

11. A reference junction for a reference electrode, said reference junction comprising a glass encasing body encasing a porous member which is a porous ceramic having a length up to one half the length of the glass encasing body, in which said glass encasing body is glass capillary tubing which is bonded to said porous member.

12. The reference junction of claim 11 wherein the encasing body is essentially a cylindrical tube.

13. The reference junction of claim 12 wherein the porous member has a length only up to one third the length of the removable encasing body.

14. The reference junction of claim 13 wherein the entire porous member is encased within the removable encasing body.

15. The reference junction of claim 14 wherein the entire porous member is encased within the tubing and one end thereof is flush with one end of the tubing.

16. The reference junction of claim 15 in which the length of said porous member is in the range of from about 1 to about 5 millimeters and the glass tubing has a length of from about 10 to about 20 millimeters.

17. The reference junction of claim 13 wherein the entire porous member is encased within the removable encasing body and one end thereof is flush with one end of the removable encasing body.

18. The reference junction of claim 11 in which the length of said porous member is in the range of from about 1 to about 5 millimeters and the glass tubing has a length of from about 10 to about 20 millimeters.

* * * * *